United States Patent
Xu

(10) Patent No.: US 10,704,025 B2
(45) Date of Patent: *Jul. 7, 2020

(54) USE OF NOGGIN, AN ALK5 INHIBITOR AND A PROTEIN KINASE C ACTIVATOR TO PRODUCE ENDOCRINE CELLS

(71) Applicant: Janssen Biotech, Inc., Horsham, PA (US)

(72) Inventor: Jean Xu, Raritan, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/457,956

(22) Filed: Mar. 13, 2017

(65) Prior Publication Data

US 2017/0183630 A1 Jun. 29, 2017

Related U.S. Application Data

(63) Continuation of application No. 14/840,297, filed on Aug. 31, 2015, now Pat. No. 9,593,310, which is a continuation of application No. 12/970,330, filed on Dec. 16, 2010, now Pat. No. 9,150,833.

(60) Provisional application No. 61/289,671, filed on Dec. 23, 2009.

(51) Int. Cl.
*C12N 5/071* (2010.01)

(52) U.S. Cl.
CPC ...... *C12N 5/0676* (2013.01); *C12N 2501/117* (2013.01); *C12N 2501/119* (2013.01); *C12N 2501/16* (2013.01); *C12N 2501/385* (2013.01); *C12N 2501/40* (2013.01); *C12N 2501/41* (2013.01); *C12N 2501/415* (2013.01); *C12N 2501/70* (2013.01); *C12N 2501/727* (2013.01); *C12N 2506/02* (2013.01); *C12N 2533/90* (2013.01)

(58) Field of Classification Search
CPC .................................................. C12N 5/0676
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder_et_al |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |

(Continued)

FOREIGN PATENT DOCUMENTS

| | | |
|---|---|---|
| CN | 1389565 A | 7/2002 |
| CN | 1602351 | 3/2005 |

(Continued)

OTHER PUBLICATIONS

D'Amour et al. (2006, Nat. Biotechnology, vol. 24(11), pp. 1392-1401) (Year: 2006).*
Lee et al. (2003, Cellular Signaling, vol. 15, pp. 529-537) (Year: 2003).*
Inman et al. (2002, Molecular Pharmacology, vol. 62(1), pp. 65-74). (Year: 2002).*
Kozikowski et al. (2003, J. Med. Chem., vol. 46, pp. 364-373). (Year: 2003).*
Ali, et al., Exploitation of Protein Kinase C: A Useful Target for Cancer Therapy, Cancer Treatment Reviews, 2009, pp. 1-8, vol. 35.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.

(Continued)

*Primary Examiner* — Thaian N Ton
*Assistant Examiner* — David A. Montanari
(74) *Attorney, Agent, or Firm* — Klarquist Sparkman, LLP

(57) ABSTRACT

The present invention provides methods to promote the differentiation of pluripotent stem cells into insulin producing cells. In particular, the present invention provides a method to produce cells expressing markers characteristic of the pancreatic endocrine lineage that co-express NKX6.1 and insulin and minimal amounts of glucagon.

19 Claims, 9 Drawing Sheets

(56) References Cited

U.S. PATENT DOCUMENTS

| | | |
|---|---|---|
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D;Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,129,182 B2 | 3/2012 | D'Amour et al. |
| 8,187,878 B2 | 5/2012 | Dalton et al. |
| 8,859,286 B2 | 10/2014 | Agulnick |
| 9,528,090 B2 | 12/2016 | Rezania |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0118148 A1 | 6/2005 | Stein et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour et al. |
| 2006/0003313 A1 | 1/2006 | D'Amour et al. |
| 2006/0003446 A1* | 1/2006 | Keller .................. C12N 5/0606 435/366 |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0141702 A1 | 6/2007 | Revazova et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1* | 7/2009 | Rezania ................ C12N 5/0676 435/377 |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0009675 A1 | 1/2012 | Martinson et al. |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |
| 2014/0186953 A1 | 7/2014 | Rezania |

FOREIGN PATENT DOCUMENTS

| | | |
|---|---|---|
| CN | 1602351 A | 3/2005 |
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| CN | 102272291 | 12/2011 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2674485 | 12/2013 |

(56) References Cited

FOREIGN PATENT DOCUMENTS

| | | |
|---|---|---|
| EP | 2479260 B1 | 6/2016 |
| GB | 2484873 B2 | 4/2014 |
| JP | 2005506074 A2 | 3/2003 |
| JP | 2005537803 A1 | 12/2005 |
| JP | 2006-500003 A2 | 1/2006 |
| JP | 2008500809 A2 | 1/2008 |
| JP | 2009513143 A2 | 4/2009 |
| JP | 2012/040025 | 1/2012 |
| KR | 10-2008-0020098 A | 3/2008 |
| RU | 2359030 C1 | 6/2009 |
| RU | 2359671 C2 | 6/2009 |
| SU | 1767433 A1 | 10/1992 |
| WO | 1996040172 A1 | 12/1996 |
| WO | 199830679 A1 | 7/1998 |
| WO | 199847892 A1 | 10/1998 |
| WO | 200029549 A1 | 5/2000 |
| WO | 200123528 A1 | 4/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO 2003/050249 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | 2004016747 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | 2004067001 A1 | 12/2004 |
| WO | 2005080598 A1 | 1/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | 2006020919 A2 | 2/2006 |
| WO | 2006088867 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006115824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007030870 A1 | 3/2007 |
| WO | 2007069666 A1 | 6/2007 |
| WO | 2007101130 A2 | 9/2007 |
| WO | WO 2007/103282 | 9/2007 |
| WO | 2007136673 A2 | 11/2007 |
| WO | 2007143193 A1 | 12/2007 |
| WO | 2008015682 A2 | 2/2008 |
| WO | WO 2009/018453 | 2/2009 |
| WO | 2009110215 A1 | 9/2009 |
| WO | 2009132083 A2 | 10/2009 |
| WO | WO 2009/132083 | 10/2009 |
| WO | 2009154606 A1 | 12/2009 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | WO 2010/051213 | 5/2010 |
| WO | WO 2010/057039 | 5/2010 |
| WO | 2011011300 A2 | 1/2011 |
| WO | 2011067465 A1 | 6/2011 |
| WO | WO 2011/079017 | 6/2011 |
| WO | WO 2011/081222 | 7/2011 |
| WO | 2011096223 A1 | 8/2011 |
| WO | 2011123572 A1 | 10/2011 |
| WO | 2011139628 A1 | 11/2011 |
| WO | WO 2011/160066 | 12/2011 |
| WO | WO 2012/030540 | 3/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.

Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.

Best, et al., Embryonic Stem Cells to Beta-Cells by Understanding Pancreas Development, Molecular and Cellular Endorinology, 2008, pp. 86-94, vol. 288.

Bo, et al., Research Progress of Pancreatic Islet Development and Pancreatic Stem Cells, Journal of Clinical Surgery, 2009, pp. 208-210, vol. 17, No. 3.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Chetty, et al., A Simple Tool ti Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

D'Amour et al, Production of pancreatic hormone, Nature Biotechnology, 2006, pp. 1392-1401, vol. 24.

Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.

Eguizabal, et al., Embryonic Stem Cells/Induced Pluriptent Stem Complete Meiosis from Human Induced Pluripotent Stem Cells, Stem Cells, 2011, pp. 1186-1195, vol. 29.

Florio, et al., Activin A Stimulates Insulin Secretion in Cultured Human Pancreatic Islets, J. Endocrinol. Invest., 2000, pp. 231-234, vol. 23.

Foster, et al., Differentiation of Transplanted Microencapsulated Fetal Pancreatic Cells, Experimental Transplantation, Jun. 15, 2007, pp. 1440-1448, vol. 83. No. 11.

Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.

(56) References Cited

OTHER PUBLICATIONS

Gibco, Solutions for Life Science Research and Drug Discovery, Catalogue Cell Culture Products, 2004-2005, pp. 1-4E, 281406 26 5 27.

Gordon Weir, Do stem cells hold the key to creation of a cure for diabetes?, Diabetes Voice, 2008, pp. 29-31, Edition 53, No. 2.

Gregg Duester, Retionoic Acid Synthesis and Signaling During Early Organogenesis, Cell, 2008, pp. 921-931, vol. 134.

Hainsworth, et al., Retinal Capillar Basement Membrane Thickening in a Porcine Model of Diabetes Mellitus, Comp Med, 2002, pp. 523-529, vol. 52.

Harmon, et al., GDF11 Modulates NGN3+ Islet Progenitor Cell Number and Promotes B-Cell Differentiation in Pancreas Development, Development, 2004, pp. 6163-6174, vol. 131.

Hay, et al., Highly Effiicient Differentiation of hESCs to Functional Hepatic Endoderm Requires ActivinA and Wnt3a Signaling, PNAS, 2008, pp. 12301-12306, vol. 105, No. 34.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Karvonen, et al., Incidene of Childhood Type 1 Diabetes Worldwide, Diabetes Care, 2000, pp. 1516-1526, vol. 23, No. 10.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Larsen, et al., Use of the Gootingen Minipig as a Model of Diabetes, with Special Focus on Type 1 Diabetes Research, ILAR Journal, 2004, pp. 303-313, vol. 45, No. 3.

Lee, et al., PKC—Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Ludwig, et al., Defined Culture Media for Human Embryonic Stem Cells, Embryonic Stem Cells, 2007, pp. 1-16, Springer.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Munoz et al, Conventional pluripotency markers, Conventional pluripotency markers, Feb. 7, 2014, pp. 1159-1164, vol. 69.

Nie, et al., Scalable Passaging of Adherent Human Pluripotent Stem Cells, PLOS One, 2014, pp. 1-9, vol. 9, Issue 1.

Ouziel-Yahalom, et al., Expansion and Redifferentiation of Adult Human Pancreatic islet Cells, Biochemical and Biophysical Research Communications, 2006, pp. 291-298, vol. 341.

Paris, et al, Embryonic Stem Cells in Domestic Animals, Embryonic Stem Cells in Domestic Animals, Feb. 7, 2014, pp. 516-524, vol. 74.

Park, et al., Effects of Activin A on Pancreatic Ductal Cells in Streptozotocin-Inducted Diabetic Rats, Experimental Transplantation, 2007, pp. 925-930, vol. 83.

Perrier, et al., Derivation of Midbrain Dopamine Neurons from Human Embryonic Stem Cells, PNAS, Aug. 24, 2004, pp. 12543-12548, vol. 101, No. 34.

Rajala, et al., Testing of Nine Different Xeno-free Culture Media for Human Embryonic Stem Cell Cultures, Human Reproduction, Jan. 24, 2007, pp. 1231-1238, vol. 22, No. 5.

Ramiya, et al., Reversal of Insulin-Dependent Diabetes Using islets Generated in vitro from Pancreatic Stem Cells, Nature Medicine, 2000, pp. 278-281, vol. 6.

Rezania, e al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.

Richards, et al., Development of Defined Media for the Serum-Free Expansion of Primary Keratinocytes and Human Embryonic Stem Cells, Tissue Engineering, 2008, pp. 221-232, vol. 14, No. 3.

Ross, et al., Cytochrome P450s in the Regulation of Cellular Retinoic Acid Metabolism, Annu. Rev. Nutr., 2011, pp. 65-87, vol. 31.

Rowley, et al., Meeting Lot-Size Challenges of Manufacturing Adherent Cells for Therapy, Cell Therapies Manufacturing, 2012, pp. 16-22, vol. 10, No. 3.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Schulz, et al., A Scalable System for Production of Functional Pancreatic Progenitors from Human Embryonic Stem Cells, PLOS One, 2012, pp. 1-17, vol. 7, Issue 5.

Simandi, et al., Retinoid Signaling is a Context-Dependent Regulator of Embryonic Stem Cells, Embryonic Stem Cells-Differentiation and Pluripotent Alternatives, 2011, pp. 55-79, Chapter 3.

Sneddon, et al., Self-Renewal of Embryonic-Stem-Cell-Derived Progenitors by Organ-Matched Mesenchyme, Nature, Nov. 29, 2012, pp. 765-770, vol. 491.

Soria, et al., From Stem Cells to Beta Cells: New Strategies in Cell Therapy of Diabetes Mellitus, Diabetologia, 2001, pp. 407-415, vol. 44.

Stacpoole, et al., Efficient Derivation of Neural Precuros Cells, Spinal Motor Neurons and Midbr, Nat Protoc, 2012, pp. 1-26, vol. 6, Issue 8.

Stafford, et al., Retinoids Signal Directly to Zebrafish Endoderm to Specify Insuilin-Expressing B-cells, Development, 2005, pp. 949-956, vol. 133.

Stoffel, et al., Navigating the Pathway from Embryonic Stem Cells to Beta Cells, Seminars in Cell & Developmental Biology, 2004, pp. 327-336, vol. 15.

Suzuken, Differentiation of Multifunctional Stem Cells Using Human Feeder Cells, Research Papers of the Suzuken Memorial Foundation, 2007, pp. 193-197, vol. 24, JP (English Abstract).

Swindle, et al., Swine in Biomedical Research: Management and Models, ILAR News, 1994, pp. 1-5, vol. 36, No. 1.

Tsuchida, et al., Activin Isoforms Signal Through Type I Receptor Serine/Threonin Kinase ALK7, Molecular and Cellular Endocrinology, 2004, pp. 59-65, vol. 22.

Vieira, et al., Modulation of Neuronal Stem Cell Differentiation by Hypoxia and Reactive Oxygen Species, Progress in Neurobiology, 2011, pp. 444-455, vol. 93.

Wang, et al., Three-Dimensional Differentiation of Embryonic Stem Cells into islet-Like Insulin-Producing Clusters, Tissue Engineering: Part A, 2009, pp. 1941-1952, vol. 15, No. 8.

Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.

White, et al., Complex Regulation of cyp26a1 Creates a Robust Retinoic Acid Gradient in the Zebrafish Embryo, PLOS Biology, 2007, pp. 2522-2533, vol. 5, Issue 11.

Xudong, et al., Research Progress in Inducing Stem Cels to Differentiate toward the B-like Cells of Pancreatic Islet, Chinese Bulletin of Life Sciences, 2007, pp. 526-530, vol. 19, No. 5 (English Abstract).

Yang, et al., Evaluation of Humam MSCs Cell Cycle, Viability and Differentiation in Micromass Culture, Biorheology, 2006, p. 489-496, vol. 43 (English Abstract).

(56) References Cited

OTHER PUBLICATIONS

Zalzman, et al., Differentiation of Human Liver-Derived, Insulin-Producing Cells Toward the B-Cell Phenotype, Diabetes, 2005, pp. 2568-2575, vol. 54.

Zuscik, et al., Regulation of Chondrogenesis and Chondrocyte Differentiation by Stress, J Clin Invest, 2008, pp. 429-438, vol. 118, Issue 2.

Abe, et al., Evidence That P13K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.

Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

Ackermann, et al., Molecular Regulation of Pancreatic B-Cell Mass Development, Maintenance, and Expansion, Journal of Molecular Endocrinology, 2007, pp. 193-206, vol. 38.

Adams, et al., Proteasome Inhibition in Cancer: Development of PS-341, Seminars in Oncology, 2001, pp. 613-619, vol. 28, No. 6.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit et al., Human Feeder Layers for Human Embryonic Stem Cells, Biology of Reproduction, Jan. 22, 2003, 2150-2156, 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Feeder Layer-and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Assady, et al., Insulin Production by Human Embryonic Stem Cells, Diabetes, 2001, pp. 1691-1697, vol. 50.

Baetge, Production of B-Cells from Human Embryonic Stem Cells, Diabetes, Obesity, Metabolism, 2008, pp. 186-194, vol. 10, Supplement 4.

Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.

Balsam, et al., Haematopoeitic Stem Cells Adopt Mature Haeatopoietic Fates in Ischaemic Myocardium, Nature, Apr. 8, 2004, pp. 668-673, ?, Nature Publishing Group.

Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

Barclay, et al., The Leucocyte Antigen Facts Book, The Leucocyte Antigen Facts Book, 1997, Textbook, 2[sup] edition, Academic Press.

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

(56) References Cited

OTHER PUBLICATIONS

Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesencymal Stem Cells in Pancreatic Islet Beta-Cells, World Journal of Gastroenterology, Oct. 15, 2004, 3016-3020, 10.
Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.
Cheon, et al., Defined Feeder-Free Culture System of Human Embryonic Stem Cells, Biol Reprod, 2005, 105.046870, DOI10/1095.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Balajthy, et al., Chapter 8. 8. Embryonic and adult stem cells in regenerative medicine I, Molecular therapies, 2011, pp. 1-6.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Brimble, S., et al., The Cell Surface Glycosphingolipids SSEA-3 and SSEA-4 Are Not Essential for Human ESC Pluripotency, Stem Cells, Jan. 2007, pp. 54-62, vol. 25, MX.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Chen, et al., Scalable GMP Compliant Suspension Culture System for Human ES Cells, Stem Cell Research, 2012, pp. 388-402, vol. 8.
Cirulli, et al., Netrins: beyond the brain, Molecular Cell Biology, Apr. 2007, pp. 296-306, vol. 8.
Cohick, et al., The Insulin-Like Growth Factors, Annual Reviews Physiol, 1993, pp. 131-153, vol. 55, Annual Reviews Inc.
Condic, et al., Alternative Sources of Pluripotent Stem Cells: Ethical and Scientific Issues Revisited, Stem Cells and Development, 2010, pp. 1121-1129, vol. 19 Issue 8, Mary Ann Liebert, Inc.
Daheron, et al., LIF/STAT3 Signaling Fails to Maintain Self-Renewal of Human Embryonic Stem Cells, Stem Cells, 2004, pp. 770-778, vol. 22.
Findikli, et al., Establishment and characterization of new human embryonic stem cell lines, Reproductive BioMedicine Online, Mar. 3, 2005, pp. 617-627, vol. 10 Issue 5.
Foster, et al., Differentiation of Transplanted Microencapsulated Fetal Pancreatic Cells, Transplantation, Jun. 15, 2007, pp. 1440-1448, vol. 83 Issue 11.
Furue, et al., Heparin promotes the growth of human embryonic stem cells in a defined serum-free medium, PNAS, Sep. 9, 2008, pp. 13409-13414, vol. 105 Issue 36.
Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir., Do stem cells hold the key to a future cure for diabetes?, Diabetes Voice, Jun. 2008, pp. 29-31, vol. 53 Issue 2.
Guillemain, et al., Glucose is Necessary for Embryonic Pancreatic Endocrine Cell Differentiation*, The Journal of Biological Chemistry, May 18, 2007, pp. 15228-15237, vol. 282 Issue 20.
Hebrok, et al., Notochord repression of endodermal Sonic hedgehog permits pancreas development, Genes & Development, Apr. 2, 1998, pp. 1705-1713, vol. 12, Issue 11, Cold Spring Harbor Laboratory Press.
Hiemisch, H., et al., Transcriptional Regulation in Endoderm Development: Characterization of an Enhancer Controlling Hnf3g Expression by Transgenesis and Targeted Mutagenesis, The EMBO Journal, 1997, 3995-4006, vol. 16(13), MX.
Jaenisch, et al., Stem Cells, the Molecular Circuitry of Pluripotency and Nuclear Reprogramming, cell, Feb. 22, 2008, pp. 567-582, vol. 132, Elsevier Inc.
Jean, et al., Pluripotent genes in avian stem cells, Development Growth & Differentiation, 2013, pp. 41-51, vol. 55.
Kang, et al., Plasma treatment of textiles—Synthetic Polymer-Based Textiles, AATCC Review, 2004, pp. 29-33, Page number.
Kehoe, et al., Scalable Stirred-Suspension Bioreactor Culture of Human Pluripotent Stem Cells, Tissue Eng Part A, 2010, pp. 405-421, vol. 16 Issue 2.
Kim, et al., Reprogrammed Pluripotent Stem Cells from Somatic Cells, International Journal of Stem Cells, 2011, pp. 1-8, vol. 4 Issue 1.
Klajnert, et al., Fluorescence studies on PAMAM dendrimers interactions with bovine serum albumin, Bioelectrochemistry, 2002, pp. 33-35, vol. 55.
Kubota, et al., Growth factors essential for self-renewal and expansion of mouse spermatogonial stem cells, cell Biology, Nov. 23, 2004, pp. 16489-16494, vol. 101, Issue 47.
Kunisada, et al., Small molecules induce efficient differentiation into insulin-producing cells from human induced pluripotent stem cells, Stem Cell Research, Oct. 11, 2011, pp. 274-284, vol. 8.
Lavial, Etal., Chicken Embryonic Stem Cells as a Non-Mammalian Embryonic Stem Cell Model, Development Growth Differentiation, Jan. 2010, pp. 101-114, vol. 52(1).
Lee, et al., Available human feeder cells for the maintenance of human embryonic stem cells, Reproduction, 2004, pp. 727-735, vol. 128.
Lin, C., et al., Coagulation Dysregulatin as a Barrier to Xenotransplantation n the Primate, Transplant Immunology, 2009, pp. 75-80, vol. 21, MX.
Ludwig, et al., Defined, Feeder-Independent Medium for human Embryonic Stem Cell Culture, Current Protocols in Stem Cell Biology, 2007, pp. 1C.2.1-1C.2.16, vol. 1, John Wiley & Sons, Inc.
Maimets, et al., Activation of p53 by nutlin leads to rapid differentiation of human embryonic stem cells, Oncogene, Jun. 2, 2008, pp. 5277-5287, vol. 27.
Maria-Jesus Obregon, Thyroid hormone and adipocyte differentiation, Thyroid, 2008, pp. 185-195, vol. 18 Issue 2.
Mcmahon, et al., Noggin-mediated antagonism of BMP signaling is required for growth and patterning of the neural tube and somite, Genes & Development, Mar. 16, 1998, pp. 1438-1452, vol. 12.
Micallef, et al., Pancreas Differentiation of Mouse ES Cells, Current Protocols in Stem Cell Biology, 2007, pp. 1G.1.1-1.2.8, John Wiley & Sons, Inc.
Misiti, et al., 3,5,30-Triiodo-L-Thyronine Enhances the Differentiation of a Human Pancreatic Duct Cell Line (hPANC-1) Towards a b-Cell-Like Phenotype, Journal of Cellular Physiology, 2005, pp. 286-296, vol. 204.
Nakanishi, et al., Pancreatic tissue formation from murine embryonic stem cells in vitro, Differentiation, 2007, pp. 1-11, vol. 75.
Nakase, et al., Myeliod Antigen, CD13, CD14, and/ or CD33 Expression is Restricted to Certain Lymphoid Neoplasms, Hematopathology, Jun. 1996, pp. 761-768, vol. 105 Issue 6.
Narang, A., et al., Biological and Biomaterial Approaches for Improved Islet Transplantation, Pharmacological Review, Jun. 2006, pp. 194-243, vol. 58(2), MX.
Nekrasov, et al., Induced pluripotent stem cells as a model for studying human diseases, Cellular Transplantology and Tissue Engineering, 2011, pp. 32-37, vol. 6 Issue 2.

(56) References Cited

OTHER PUBLICATIONS

Nostro, et al., Generation of Beta Cells from Human Pluripotent Stem Cells: Potential for Regenerative Medicine, Seminars in Cell & Developmental Biology, 2012, pp. 701-710, vol. 23.

Olmer, et al., Long Term Expansion of Undifferentiated Human iPS and ES Cells in Suspension Culture Using Defined Medium, Stem Cell Research, 2010, pp. 51-64, vol. 5.

Osafune, et al., Marked differences in differentiation propensity among human embryonic stem cell lines, Nature Biotechnology, Feb. 17, 2008, pp. 313-315, vol. 26 Issue 3.

Ouziel-Yahalom, et al., Expansion and redifferentiation of adult human pancreatic islet cells, Biochemical and Biophysical Research Communications, Jan. 19, 2006, pp. 291-298, vol. 341.

Petitte, J., et al., Avian Pluripotent Stem Cells, Mechanisms of Development, 2004, pp. 1159-1168, vol. 121, MX.

Ramiya, et al., Reversal of insulin-dependent diabetes using islets generated in vitro from pancreatic stem cells, Nature Medicine, Mar. 2000, pp. 278-282, vol. 6 Issue 3.

Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytochemistry, 1986, pp. 527-533, vol. 34 , Issue 4.

Rezania, et al., Reversal of Diabetes with Insulin-Producing Cells Derived in vitro from Human Pluripotent Stem Cells, Nature Biotechnology, 2014, pp. 1121-1133, vol. 32, No. 11.

Rother, et al., Challenges facing islet transplantation for the treatment of type 1 diabetes mellitus, The Journal of Clinical Investigation, 2004, pp. 877-883, vol. 114 Issue 7.

Rowely, et al., Meeting Lot-size Challenges of Manufacturing Adherent Cells for Therapy, Bio Process International, Mar. 2012, pp. 16-22, vol. 10 Issue 3.

Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182 , Issue 2.

Sigma-Aldrich, Sigma-Aldrich Inc., Sigma-Aldrich, 2007, pp. 1-2, page number.

Sjogren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.

Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.

Suzuken., Differentiation of Multifunctional Stem Cells Using Human Feeder Cells, Research Papers of the Suzuken Memorial Foundation, 2007, pp. 193-197, vol. 2.

Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.

Thomson, Bioprocessing of Embryonic Stem Cells for Drug Discovery, Trends in Biotechnology, 2007, pp. 224-230, vol. 25, No. 5.

Verkhovskaya, et al., Effect of alkoxy-substituted of glycerin on the morphofunctional properties of continuous cell culture, Cryobiology, 1990, pp. 30-33, vol. 1.

Wachs, et al., High Efficacy of Clonal Growth and Expansion of Adult Neural Stem Cells, Laboratory Investigation, 2003, pp. 949-962, vol. 83, No. 7.

Wang, et al., Cultivation and identification of pancreatic endocrine progenitor cells, National Medical Journal of China, 2006, pp. 1850-1853, vol. 86 Issue 26.

Wang, et al., Scalable expansion of human induced pluripotent stem cells in the defined xeno-free E8 medium under adherent and suspension culture conditions, Stem Cell Research, Nov. 2013, pp. 1103-1116, vol. 11 Issue 3.

Yadlin, et al., Small-molecule inducers of insulin expression in pancreatic α-cells, PNAS, Aug. 24, 2010, pp. 15099-15104, vol. 107 Issue 34.

Yang JW, et al., Evaluation of human MSCs cell cycle, viability and differentiation in micromass culture, Biorheology, 2006, pp. 1-2, vol. 43 Issue (3-4).

Yim,et al., Proliferation and differentiation of human embryonic germ cell derivatives in bioactive polymeric fibrous scaffold, J.Biomater. Sci.Polymer Edn,, Jan. 19, 2005, pp. 1193-1217, vol. 16 Issue 10.

Zhu, et al., A Small Molecule Primes Embryonic Stem Cells for Differentiation, Cell Stem Cell, May 8, 2009, pp. 416-426, vol. 4.

Zulewski, et al., Multipotentital Nestin-Positive Stem Cells Isolated From Adult Pancreatic Islets Differentiate Ex Vivo Into Pancreatic Endocrine, Exocrine, and Hepatic Phenotypes, Diabetes, 2001, pp. 521-533, vol. 50.

Bose et al., "Human embryonic stem cell differentiation into insulin secreting b-cells for diabetes, Cell Biology Intl., 2012, pp. 1013-1020," vol. 36, No. 11.

Cai et al., "Prospectively Isolated NGN3-Expressing Progenitors from Human Embryonic Stem Cells give Rise to Pancreatic Endocrine Cells," Stem Cells Translational Medicine, e-pub, Feb. 2014, pp. 489-499, vol. 3, No. 4.

D'Amour et al., "Production of pancreatic hormone—expressing endocrine cells from human embryonic stem cells," Nature Biotechnology, Oct. 19, 2006, 1392-1401, vol. 24 Issue 11.

Jennings et al., "Development of the Human Pancreas from Foregut to Endocrine Commitment," Diabetes, 2013, pp. 3514-3522, vol. 62, No. 10.

Jiang, et al., "Generation of Insulin-Producing Islet-Like Clusters from Human Embryonic Stem Cells," 2007, Stem Cells, pp. 1940-1953, vol. 25.

Jiang, et al., "In Vitro Derivation of Functional Insulin-Producing Cells from Human Embryonic Stem Cells," Cell Research, 2007, pp. 333-344, vol. 17.

Kroon, et al., "Pancreatic Endoderm Derived from Human Embryonic Stem Cells Generates Glucose-Responsive Insulin-Secreting Cells in vivo," Nature Biotechnology, Apr. 2008, pp. 443-452, vol. 26, No. 4.

Pagliuca et al., "How to Make a Functional Beta-Cell, Development," 2013, pp. 2472-2483, vol. 140, No. 2.

Segev, et al., "Differentiation of Human Embryonic Stem Cells into Insulin-Producing Clusters," Stem Cells, Jan. 1, 2004, pp. 265-274.

Zhang et al, "Highly Efficient Differentiation of Human ES Cells and iPS Cells into Mature Pancreatic Insulin-Producing Cells," Cell Research, 2009, pp. 429-438, vol. 19, Issue 4.

\* cited by examiner

USE OF NOGGIN, AN ALK5 INHIBITOR AND A PROTEIN KINASE C ACTIVATOR TO PRODUCE ENDOCRINE CELLS

This is application a continuation application of U.S. patent application Ser. No. 14/840,297, filed on Aug. 31, 2015 (now U.S. Pat. No. 9,593,310, issued Mar. 14, 2017), which is a continuation application of U.S. patent application Ser. No. 12/970,330, filed on Dec. 16, 2010 (now U.S. Pat. No. 9,150,833, issued Oct. 6, 2015), which claims the benefit of U.S. Provisional Application No. 61/289,671, filed on Dec. 23, 2009, which are hereby incorporated by reference herein in their entirety.

FIELD OF THE INVENTION

The present invention provides methods to promote the differentiation of pluripotent stem cells into insulin producing cells. In particular, the present invention provides a method to produce cells expressing markers characteristic of the pancreatic endocrine lineage that co-express NKX6.1 and insulin and minimal amounts of glucagon.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form PDX1 positive pancreatic endoderm. Retinoic acid is most effective at inducing Pdx1 expression when added to cultures at day 4 of embryonic stem cell differentiation during a period corresponding to the end of gastrulation in the embryo (Diabetes 54:301, 2005).

Miyazaki et al. reports a mouse embryonic stem cell line over-expressing Pdxl. Their results show that exogenous Pdx1 expression clearly enhanced the expression of insulin, somatostatin, glucokinase, neurogenin3, p48, Pax6, and Hnf6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into PDX1 positive cells. They observed that TGF-β2 reproducibly yielded a higher proportion of PDX1 positive cells (Genes Cells. 2005 June; 10(6): 503-16.).

Gordon et al. demonstrated the induction of brachyury [positive]/HNF3 beta [positive] endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into PDX1 positive cells after addition of FGF-10 (US 2005/0266554A1).

D'Amour et al. (Nature Biotechnology 24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate PDX1 positive cells. The terminal differentiation was induced by nicotinamide.

In one example, Benvenistry et al. states: "We conclude that over-expression of PDX1 enhanced expression of pancreatic enriched genes, induction of insulin expression may require additional signals that are only present in vivo" (Benvenistry et al., Stem Cells 2006; 24:1923-1930).

In another example, Grapin-Botton et al. states: "Early activation of Ngn3 almost exclusively induced glucagon+ cells while depleting the pool of pancreas progenitors. As from E11.5, PDX-1 progenitors became competent to differentiate into insulin [positive] and PP [positive] cells" (Johansson K A et al., Developmental Cell 12, 457-465, March 2007).

For example, Diez et al. states; "At 9 and 10 weeks, most of the glucagon positive cells co-expressed insulin, although distinct insulin-only cells were clearly detectable at these stages. Cells co-expressing insulin and glucagon were observed during the whole period studies (9 to 21 weeks) but they represent merely a small fraction of the total insulin and glucagon expressing cells." (J Histochem Cytochem. 2009 September; 57(9):811-24. 2009 Apr. 13.)

In one example, Chen et al. states ""(−)-indolactam V [(ILV)] activates protein kinase C signaling and directs the pancreatic specification of hESCs that have already been committed to the endoderm lineage . . . ILV and retinoic acid function through a related mechanism . . . ILV shows a stronger induction of PDX-1 expressing cells (percentage of cells expressing PDX-1) than does retinoic acid." (Nature Chemical Biology 5, 195-196 (April 2009) doi:10.1038/nchembio0409-195).

Lyttle et al. states: "NKX6-1 co-localised only with insulin cells, indicating that NKX6-1 is exclusively involved in human beta cell development." (Diabetologia 2008 July: 51(7):1169-80, 2008).

Therefore, there still remains a significant need to develop in vitro methods to generate a functional insulin expressing cell, that more closely resemble a β cell. The present invention takes an alternative approach to improve the efficiency of differentiating human embryonic stem cells toward insulin expressing cells, by generating a population of cells expressing markers characteristic of the pancreatic endocrine lineage that co-express NKX6.1 and insulin and minimal amounts of glucagon.

SUMMARY

In one embodiment, the present invention provides a population of cells expressing markers characteristic of the pancreatic endocrine lineage that co-express NKX6.1 and insulin and minimal amounts of glucagon.

In one embodiment, the present invention provides a method to differentiate a population of pluripotent stem cells into a population of cells expressing markers characteristic of the pancreatic endocrine lineage that co-express NKX6.1 and insulin and minimal amounts of glucagon, comprising the steps of:

a. Culturing the pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage that co-express NKX6.1 and insulin and minimal amounts of glucagon, by treating the cells expressing markers characteristic of the pancreatic endoderm lineage with medium supplemented with a protein kinase C activator.

DETAILED DESCRIPTION

Figure 1:
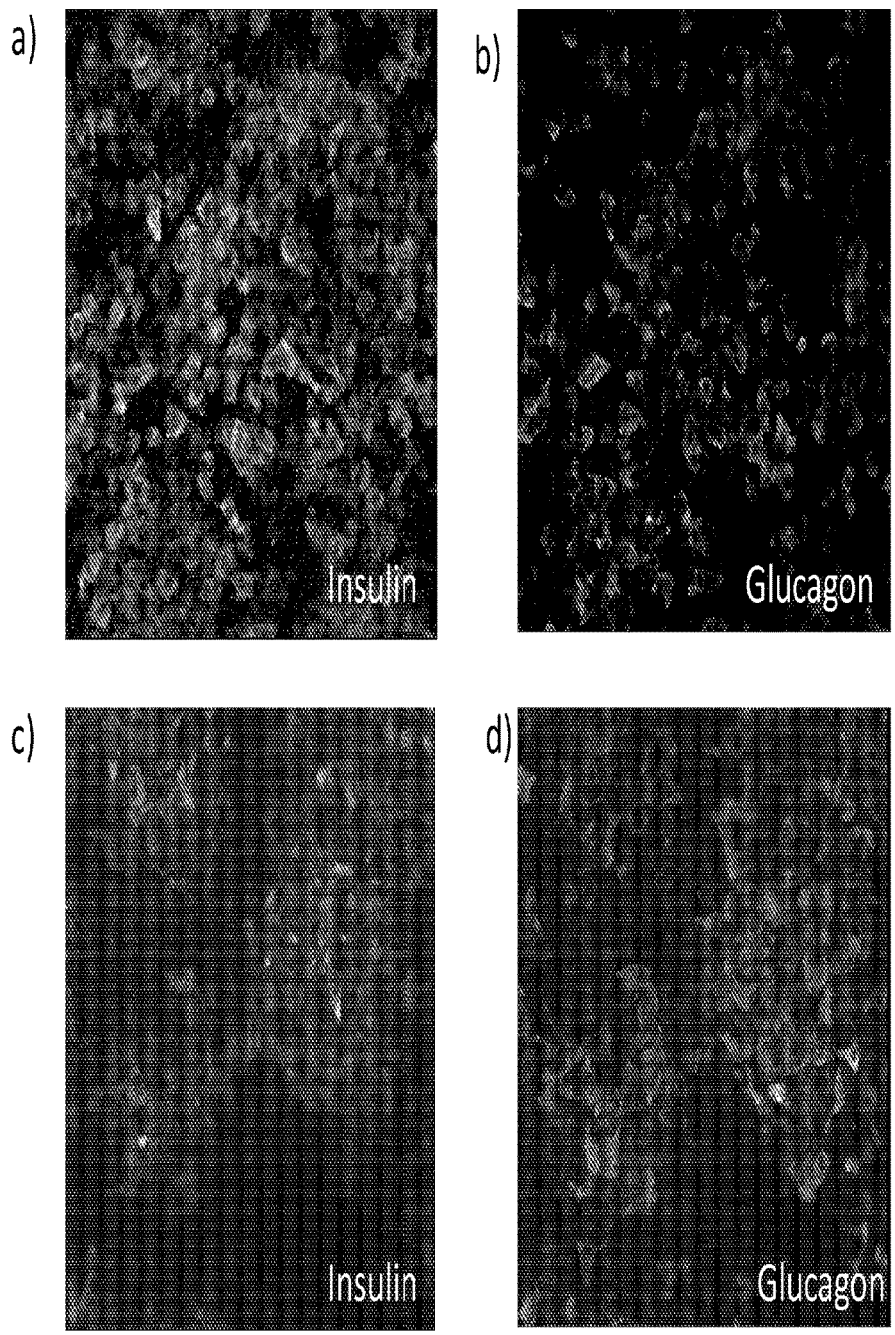
FIG. 1 shows the effect of TPB treatment on the expression of insulin and glucagon in the cells of the present invention. Panels a and b show the expression of insulin and glucagon respectively, in cells treated with TPB. Control populations of cells are shown in panels c and d.

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Cells expressing markers characteristic of the definitive endoderm lineage", or "Stage 1 cells", or "Stage 1", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage include pancreatic endoderm cells, primitive gut tube cells, and posterior foregut cells.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, and MIXL1.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Pancreatic endocrine cell", or "Pancreatic hormone expressing cell", or "Cells expressing markers characteristic of the pancreatic endocrine lineage" as used herein, refers to a cell capable of expressing at least one of the following hormones: insulin, glucagon, somatostatin, and pancreatic polypeptide.

Isolation, Expansion and Culture of Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra 1-60, and Tra 1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10 to 12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al. (Nature Biotechnology 18: 399-404 (2000)) and Thompson et al. (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al., (Stem Cells 21: 546-556, 2003) evaluated a panel of 11 different human adult, fetal and neonatal feeder cell layers for their ability to support human pluripotent stem cell culture. Richards et al., states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al. (Stem Cells 23: 1221-1227, 2005) discloses methods for the long-term growth of human pluripotent stem cells on feeder cell layers derived from human embryonic stem cells.

In another example, Stojkovic et al. (Stem Cells 2005 23: 306-314, 2005) disclose a feeder cell system derived from the spontaneous differentiation of human embryonic stem cells.

In a further example, Miyamoto et al. (Stem Cells 22: 433-440, 2004) disclose a source of feeder cells obtained from human placenta.

Amit et al. (Biol. Reprod 68: 2150-2156, 2003) discloses a feeder cell layer derived from human foreskin.

In another example, Inzunza et al. (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells; in particular, those differentiated and immortalized transgenic hepatocytes, named MMH (Met Murine Hepatocyte)."

In another example, Xu et al. (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al. (BioReprod DOI: 10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al. (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, a suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Formation of Cells Expressing Markers Characteristic of the Pancreatic Endocrine Lineage from Pluripotent Stem Cells In one embodiment, the present invention provides a method for producing cells expressing markers characteristic of the pancreatic endoderm lineage from pluripotent stem cells, comprising the steps of:
a. Culturing pluripotent stem cells,
b. Differentiating the pluripotent stem cells into cells expressing markers characteristic of the definitive endoderm lineage,
c. Differentiating the cells expressing markers characteristic of the definitive endoderm lineage into cells expressing markers characteristic of the pancreatic endoderm lineage, and
d. Differentiating the cells expressing markers characteristic of the pancreatic endoderm lineage into cells expressing markers characteristic of the pancreatic endocrine lineage.

In one aspect of the present invention, the cells expressing markers characteristic of the pancreatic endocrine lineage co-express NKX6.1 and insulin and minimal amounts of glucagon.

Differentiation of Pluripotent Stem Cells into Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically minimal amounts of such markers. Thus, differentiation of pluripotent cells is detected when cells begin to express them.

Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al., Nature Biotechnology 23, 1534-1541 (2005).

For example, pluripotent stem cells may be differentiated into cells expressing markers characteristic of the definitive endoderm lineage according to the methods disclosed in Shinozaki et al., Development 131, 1651-1662 (2004).

For example, pluripotent stem cells may be differentiated into cells expressing markers characteristic of the definitive endoderm lineage according to the methods disclosed in McLean et al., Stem Cells 25, 29-38 (2007).

For example, pluripotent stem cells may be differentiated into cells expressing markers characteristic of the definitive endoderm lineage according to the methods disclosed in D'Amour et al., Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al., Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

For example, pluripotent stem cells may be differentiated into cells expressing markers characteristic of the definitive endoderm lineage by treating the pluripotent stem cells according to the methods disclosed in U.S. patent application Ser. No. 11/736,908, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 60/990,529.

For example, pluripotent stem cells may be differentiated into cells expressing markers characteristic of the definitive endoderm lineage by treating the pluripotent stem cells according to the methods disclosed in U.S. patent application Ser. No. 61/076,889.

For example, pluripotent stem cells may be differentiated into cells expressing markers characteristic of the definitive endoderm lineage by treating the pluripotent stem cells according to the methods disclosed in U.S. patent application Ser. No. 61/076,900.

For example, pluripotent stem cells may be differentiated into cells expressing markers characteristic of the definitive endoderm lineage by treating the pluripotent stem cells according to the methods disclosed in U.S. patent application Ser. No. 61/076,908.

For example, pluripotent stem cells may be differentiated into cells expressing markers characteristic of the definitive endoderm lineage by treating the pluripotent stem cells according to the methods disclosed in U.S. patent application Ser. No. 61/076,915.

Differentiation of Cells Expressing Markers Characteristic of the Definitive Endoderm Lineage into Cells Expressing Markers Characteristic of the Pancreatic Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al., Nature Biotechnol. 24:1392-1401, 2006.

In one embodiment, the cells expressing markers characteristic of the pancreatic endoderm lineage co-express PDX1, NKX6.1, but minimal amounts of CDX2 and NGN3.

In one embodiment, cells expressing markers characteristic of the definitive endoderm lineage are differentiated into cells expressing markers characteristic of the pancreatic endoderm lineage that co-express PDX1, NKX6.1, but minimal amounts of CDX2 and NGN3, by culturing the cells expressing markers characteristic of the definitive endoderm lineage in a first medium supplemented with FGF7, followed by culturing the cells in a second medium supplemented with FGF7, a factor capable of inhibiting BMP, a TGFβ receptor agonist, retinoic acid, and a hedgehog signaling pathway inhibitor.

In one embodiment, FGF7 may be used at a concentration from about 50 pg/ml to about 50 µg/ml. In one embodiment, FGF7 is used at a concentration of 50 ng/ml.

In one embodiment, the factor capable of inhibiting BMP is noggin. Noggin may be used at a concentration from about 500 ng/ml to about 500 µg/ml. In one embodiment, noggin is used at a concentration of 100 ng/ml.

In one embodiment, the TGFβ receptor agonist is selected from the group consisting of activin A, activin B, TGFβ-I, TGFβ-II, GDF-8, and GDF-11.

Activin A may be used at a concentration from about 2 ng/ml to 100 ng/ml. In one embodiment, activin A is used at a concentration of 20 ng/ml. In an alternate embodiment, activin A is used at a concentration of 50 ng/ml.

Activin B may be used at a concentration from about 2 ng/ml to 100 ng/ml. In one embodiment, activin B is used at a concentration of 20 ng/ml. In an alternate embodiment, activin B is used at a concentration of 50 ng/ml.

TGFβ-I may be used at a concentration from about 2 ng/ml to 100 ng/ml. In one embodiment, TGFβ-I is used at a concentration of 20 ng/ml. In an alternate embodiment, TGFβ-I is used at a concentration of 50 ng/ml.

TGFβ-II may be used at a concentration from about 2 ng/ml to 100 ng/ml. In one embodiment, TGFβ-II is used at a concentration of 20 ng/ml. In an alternate embodiment, TGFβ-II is used at a concentration of 50 ng/ml.

GDF-8 may be used at a concentration from about 2 ng/ml to 100 ng/ml. In one embodiment, GDF-8 is used at a concentration of 20 ng/ml. In an alternate embodiment, GDF-8 is used at a concentration of 50 ng/ml.

GDF-11 may be used at a concentration from about 2 ng/ml to 100 ng/ml. In one embodiment, GDF-11 is used at a concentration of 20 ng/ml. In an alternate embodiment, GDF-11 is used at a concentration of 50 ng/ml.

Retinoic acid may be used at a concentration from about 1 nM to about 1 mM. In one embodiment, retinoic acid is used at a concentration of 1 µM.

In one embodiment, the hedgehog signaling pathway inhibitor is cyclopamine-KAAD. Cyclopamine-KAAD may be used at a concentration from about 0.025 µM to about 2.5 µM. In one embodiment, cyclopamine-KAAD is used at a concentration of 0.25 µM.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, Nanog, hTERT, UTF1, ZFP42, SSEA-3, SSEA-4, Tra 1-60, Tra 1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, cripto, CD9, FOXD3, CONNEXIN43, CONNEXIN45, OCT4, SOX2, Nanog, hTERT, UTF1, ZFP42, SSEA-3, SSEA-4, Tra 1-60, and Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4, CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, NKX6.1, HNF1 beta, PTF1 alpha, HNF6, HNF4 alpha, SOX9, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Differentiation of Cells Expressing Markers Characteristic of the Pancreatic Endoderm Lineage into Cells Expressing Markers of the Pancreatic Endocrine Lineage In one embodiment, cells expressing markers characteristic of the pancreatic endoderm lineage are further differentiated into cells expressing markers characteristic of the pancreatic endocrine lineage.

In one embodiment, the cells expressing markers characteristic of the pancreatic endoderm lineage co-express PDX1, NKX6.1, but minimal amounts of CDX2 and NGN3.

In one embodiment, the cells expressing markers characteristic of the pancreatic endocrine lineage co-express NKX6.1 and insulin and minimal amounts of glucagon.

In one embodiment, cells expressing markers characteristic of the pancreatic endoderm lineage are differentiated into cells expressing markers characteristic of the pancreatic endocrine lineage that co-express NKX6.1 and insulin and minimal amounts of glucagon, by culturing the cells expressing markers characteristic of the pancreatic endoderm lineage in a medium supplemented with a factor capable of inhibiting BMP, a TGFβ receptor signaling inhibitor, and a protein kinase C activator.

In one embodiment, the factor capable of inhibiting BMP is noggin. Noggin may be used at a concentration from about 500 ng/ml to about 500 µg/ml. In one embodiment, noggin is used at a concentration of 100 ng/ml.

In one embodiment, the TGFβ receptor signaling inhibitor is an inhibitor of ALK5. In one embodiment, the inhibitor of ALK5 is ALK5 inhibitor II. The ALK5 inhibitor II may be used at a concentration from about 0.1 µM to about 10 µM. In one embodiment, ALK5 inhibitor II is used at a concentration of 1 µM.

In one embodiment, the protein kinase C activator is selected from the group consisting of (2S, 5S)-(E, E)-8-(5-(4-(Trifluoromethyl)phenyl)-2,4-pentadiemoylamino) benzolactam, Indolactam V, and phorbol-12-myristate-13-acetate. In one embodiment, the protein kinase C activator is (2S, 5S)-(E, E)-8-(5-(4-(Trifluoromethyl)phenyl)-2,4-pentadiemoylamino) benzolactam. (2S, 5S)-(E, E)-8-(5-(4-(Trifluoromethyl)phenyl)-2,4-pentadiemoylamino) benzolactam may be used at a concentration from about 20 nM to about 500 nM. (2S, 5S)-(E, E)-8-(5-(4-(Trifluoromethyl)phenyl)-2,4-pentadiemoylamino) benzolactam, Indolactam V, and phorbol-12-myristate-13-acetate is referred to herein as "TPB".

Markers characteristic of the pancreatic endocrine lineage are selected from the group consisting of NEUROD, ISL1, PDX1, NKX6.1, NKX2.2, PAX4, and PAX6. In one embodiment, the cells expressing markers characteristic of the pancreatic endocrine lineage co-express NKX6.1 and insulin and minimal amounts of glucagon.

Therapies

In one aspect, the present invention provides a method for treating a patient suffering from, or at risk of developing, Type1 diabetes. In one embodiment, the method involves culturing pluripotent stem cells, differentiating the pluripotent stem cells in vitro into cells expressing markers characteristic of the pancreatic endocrine lineage, and implanting the cells expressing markers characteristic of the pancreatic endocrine lineage into a patient.

In yet another aspect, this invention provides a method for treating a patient suffering from, or at risk of developing, Type 2 diabetes. In one embodiment, the method involves culturing pluripotent stem cells, differentiating the pluripotent stem cells in vitro into cells expressing markers characteristic of the pancreatic endocrine lineage, and implanting the cells expressing markers characteristic of the pancreatic endocrine lineage into a patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells, prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a β-cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770, 417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

EXAMPLES

Example 1

Formation of a Population of Cells Expressing Markers Characteristic of the Pancreatic Endocrine Lineage that Co-Express Insulin and NKX6.1 and Minimal Amounts of Glucagon Cells of the human embryonic stem cells line H1 were cultured on MATRIGEL® (1:30 dilution) (BD Biosciences; Cat #356231)-coated dishes with RPMI medium (Invitrogen; Cat #: 22400)+0.2% FBS+100 ng/ml activin A (PeproTech; Cat #120-14)+20 ng/ml WNT-3a (R&D Systems; Cat #1324-WN/CF) for one day followed by treatment with RPMI media+0.5% FBS+100 ng/ml activin A for an additional two days (Stage 1), then,
    DMEM/F12 (Invitrogen; Cat #11330-032)+2% FBS+50 ng/ml FGF7 (PeproTech; Cat #100-19) for three days (Stage 2), then
    DMEM-High glucose (Invitrogen; Cat #10569)+1% B27+50 ng/ml FGF7+0.25 µM Cyclopamine-KAAD (Calbiochem; Cat #239804)+100 ng/ml Noggin (R&D Systems; Cat #3344-NG) for four days (Stage 3), then
    DMEM-High glucose+1% B27 (Invitrogen; Cat #0791)+100 ng/ml Noggin+1 µM ALK5 inhibitor II (Axxora; Cat #ALX-270-445)+500 nM TBP ((2S, 5S)-(E, E)-8-(5-(4-(Trifluoromethyl)phenyl)-2,4-pentadiemoylamino) benzolactam) (Calbiochem; Cat #565740) for six days (Stage 4).

As a control, separate populations of cells were treated with DMEM-High glucose+1% B27+100 ng/ml Noggin+1 µM ALK5 inhibitor II for six days (Stage 4, control group).

Figure 5:
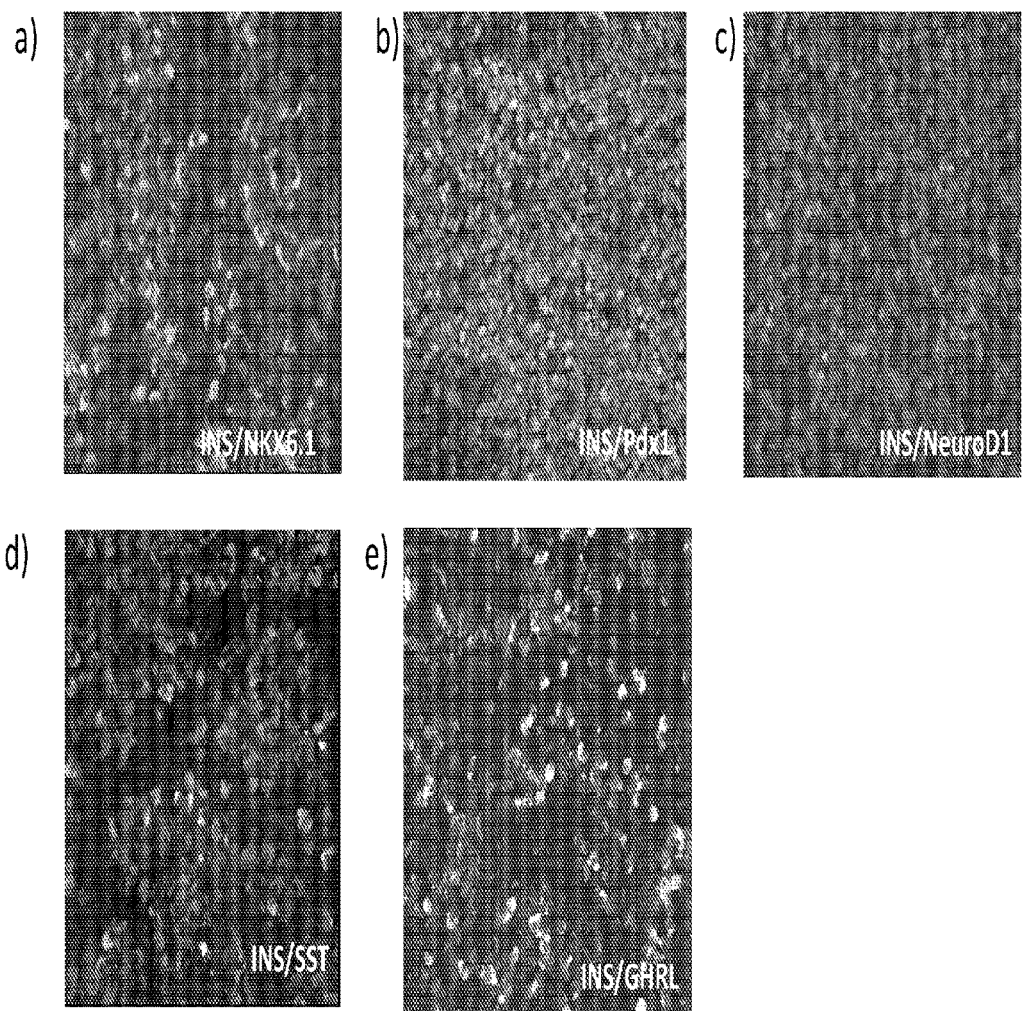
FIG. 5 shows the expression of markers characteristic of the pancreatic endocrine lineage in cells treated according to the methods of the present invention. The panels depict the expression of insulin and NKX6.1 (panel a), insulin and PDX1 (panel b), insulin and NEUROD1 (panel c), insulin and somatostatin (panel d), and insulin and ghrelin (panel e).

As shown in FIG. 1, TBP treatment at stage 4 resulted in an increase of insulin-expressing cells (FIG. 1 panel a). It was noted that about 60% of these insulin expressing cells are single endocrine hormone expressing cells, wherein the cells expressed insulin and did not express glucagon somatostatin and ghrelin (FIG. 1 panel a and b, FIG. 5 panel d and e). Glucagon-expressing cells were also noted in the cultures that received TBP treatment. Most of the glucagon-expressing cells also co-expressed insulin (FIG. 1 panel a and b). For the control group, the majority of the cells co-expressed insulin and glucagon (FIG. 1 panel c and d).

In a separate experiment, cells of the human embryonic stem cells line H1 were cultured on MATRIGEL® (1:30 dilution) coated dishes with RPMI medium+0.2% FBS+100 ng/ml activin A+20 ng/ml WNT-3a for one day followed by treatment with RPMI media+0.5% FBS+100 ng/ml activin A for an additional two days (Stage 1), then
  a. DMEM/F12+2% FBS+50 ng/ml FGF7 for three days (Stage 2), then
  b. DMEM-High glucose+1% B27+0.25 µM Cyclopamine-KAAD+2 µM Retinoic acid (RA)+100 ng/ml of Noggin for four days (Stage 3), then
  c. Treatment 1: DMEM-High glucose+1% B27+100 ng/ml Noggin+1 µM ALK5 inhibitor II+500 nM TBP for six days (Stage 4, Treatment 1), or
  d. Treatment 2: DMEM-High glucose+1% B27+100 ng/ml Noggin+1 µM ALK5 inhibitor II+100 nM TBP for six days (Stage 4, Treatment 2), or
  e. Treatment 3: DMEM-High glucose+1% B27+100 ng/ml Noggin+1 µM ALK5 inhibitor II+20 nM TBP for six days (Stage 4, Treatment 3), or
  f. Treatment 4: DMEM-High glucose+1% B27+100 ng/ml Noggin+1 µM ALK5 inhibitor II for six days (Stage 4, Treatment 4).

Figure 2:
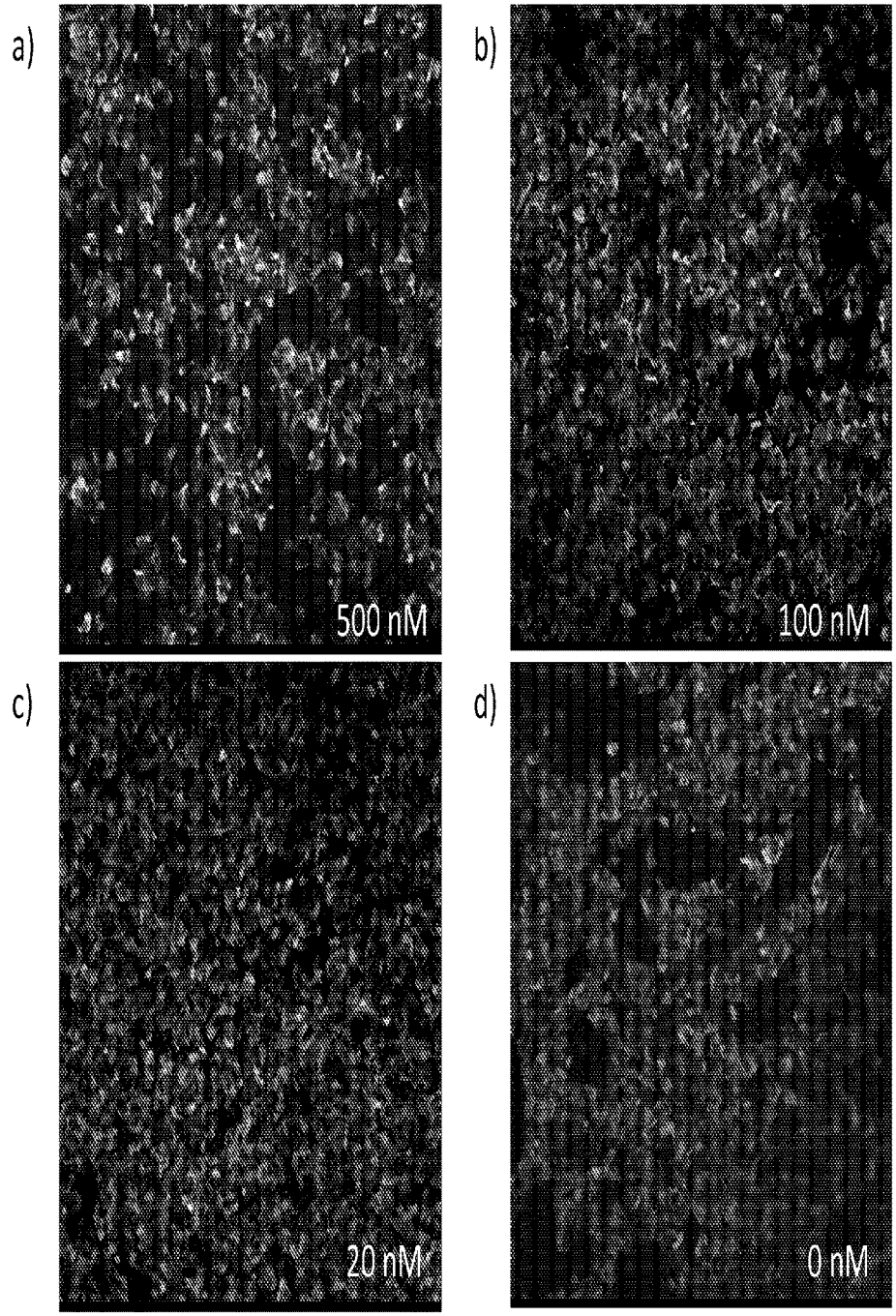
FIG. 2 shows the effect of various concentrations of TPB on the expression of insulin and glucagon in cells treated according to the methods of the present invention. Panels a through d show the expression of insulin and glucagon in populations of cells treated with TPB at the doses indicated.

Immunocytochemistry analysis was used to assess the effects of the different concentrations of TPB on the formation of the cells of the present invention. Significant increases in the number of single insulin-expressing cells was observed in both 500 nM and 100 nM TPB treatment groups (FIG. 2 panel a and b). FACS analysis confirmed that both treatments gave rise to 12% single insulin expressing cells in vitro and 15% of that population also expressed NKX6.1 (Table 1—NKX6.1/INS expressing cells were 2.4% of the total population). At 20 nM TPB, similar to the control group, most cells co-expressed insulin and glucagon (FIG. 2 panel c and d).

TABLE 1

Expression of markers characteristic of the pancreatic endocrine lineage, shown as a percentage of the total cell population.

| | Synaptophysin | INS | NKX6.1 | NKX6.1/INS |
|---|---|---|---|---|
| TPB (500 nM) | 38.3% | 9.4% | 45.7% | 2.4% |
| TPB (100 nM) | 47.6% | 14.4% | 34.8% | 3.1% |

In order to further confirm that the effect on endocrine hormone expressing cell formation was mediated by the activation of protein kinase C, separate populations of cells of the human embryonic stem cells line H1 were cultured on MATRIGEL® (1:30 dilution) coated dishes with RPMI medium+0.2% FBS+100 ng/ml activin A+20 ng/ml WNT-3a for one day followed by treatment with RPMI media+0.5% FBS+100 ng/ml activin A for an additional two days (Stage 1), then
    DMEM/F12+2% FBS+50 ng/ml FGF7 for three days (Stage 2), then
    DMEM-High glucose+1% B27+0.25 µM Cyclopamine-KAAD+2 µM Retinoic acid (RA)+100 ng/ml of Noggin for four days (Stage 3), then
    Treatment 5: DMEM-High glucose+1% B27+100 ng/ml Noggin+1 µM ALK5 inhibitor II+500 nM TBP for six days (Stage 4, Treatment 5), or
    Treatment 6: DMEM-High glucose+1% B27+100 ng/ml Noggin+1 µM ALK5 inhibitor II+500 nM TPB+5 µM GÖ 6976 for six days (Stage 4, Treatment 6), or Treatment 7: DMEM-High glucose+1% B27+100 ng/ml Noggin+1 μM ALK5 inhibitor II (Stage 4, Treatment 7), then DMEM-High glucose+1% B27 for four days (Stage 5).

Figure 3:
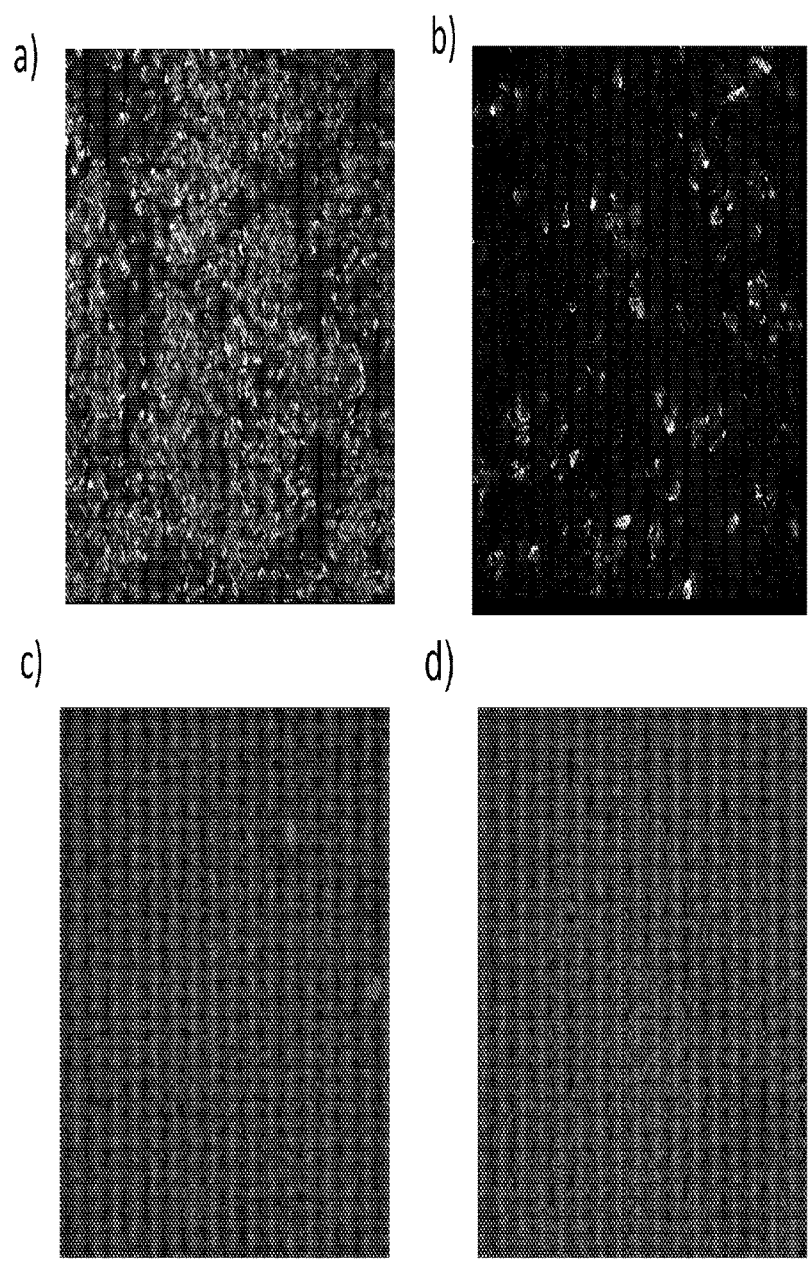
FIG. 3 shows the effect of a protein kinase C inhibitor on the expression of insulin and glucagon in cells treated according to the methods of the present invention. Panel a depicts the expression of insulin and glucagon in cells treated with TPB, and Panel c depicts the corresponding DAPI staining). Panel b depicts the expression of insulin and glucagon in cells treated with TPB and GO 6976, and Panel d depicts the corresponding DAPI staining).

GÖ 6976 is known to selectively inhibit $Ca^{2+}$-dependent protein kinase C isoforms. A significant decrease in the number cells expressing markers characteristic of the pancreatic endocrine lineage, in cultures receiving TPB alone (FIG. 3, panel a) and TPB and GÖ 6976 (FIG. 3, panel b). FACS analysis confirmed that TPB treatment (Treatment 6) gave rise to 30.6% synaptophysin, 12% single insulin and 4.6% glucagon expressing cells. On the other hand, TBP and GÖ 6976 treatment (Treatment 7) gave rise to 10.6% synaptophysin and no detectable level of single insulin expressing cells (Table 2). There was no difference in the total number of cells observed between Treatment 6 and Treatment 7. (See FIG. 3, panels c and d, showing DAPI staining, reflecting total cell number in Treatment 6 and Treatment 7). These results suggest that protein kinase C signaling may be important for the formation of cells expressing markers characteristic of the pancreatic endocrine lineage.

Figure 4:
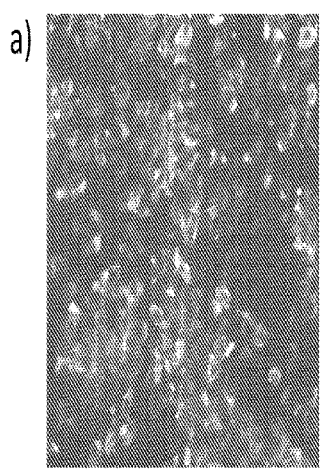
FIG. 4 shows the effect of various protein kinase C activators on the expression of insulin in cells treated according to the methods of the present invention. Panel a shows the expression of insulin in cells treated with TPB. Panel b shows the expression of insulin in cells treated with ILV. Panel c shows the expression of insulin in cells treated with PMA.
Figure 4:
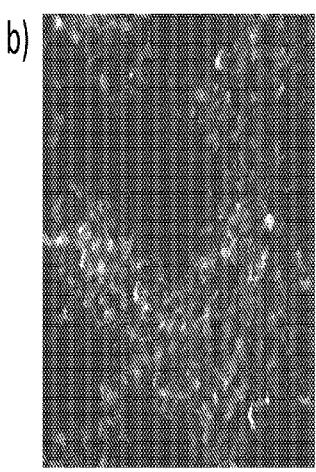
Figure 4:
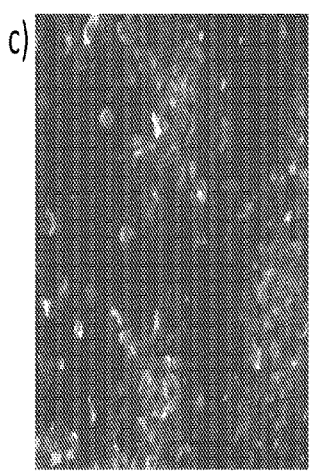

Other protein kinase C activators were also tested. These were Indolactam V (ILV) (Axxora; Cat #ALX-420-011-C300) and phorbol-12-myristate-13-acetate (PMA) (Calbiochem; Cat#524400). However, only TPB demonstrated the formation of single insulin expressing cells (FIG. 4, panel a). Both ILV (FIG. 4, panel b) and PMA (FIG. 4, panel c) at 500 nM, gave rise to cells co-expressing insulin and glucagon after six days. FACS analysis confirmed that TPB treatment gave rise to 12% single insulin expressing, and 4.6% glucagon expressing cells and 7.1% insulin and glucagon co-expressing cells. On the other hand, ILV treatment gave rise to 3% single insulin expressing, and 12% glucagon cells and 12% insulin and glucagon co-expressing cells (Table 2). Immunocytochemistry analysis showed that in cultures treated with TPB, 20% of the insulin expressing cells co-expressed NKX6.1 (FIG. 5 panel a) and PDX1 (FIG. 5 panel b). The majority of the insulin expressing cells co-expressed NEUROD, an endocrine maker (FIG. 5 panel c). Very few of the insulin expressing cells co-expressed somatostatin or ghrelin (GHRL) (FIG. 5 panel d and e).

TABLE 2

Expression of markers characteristic of the pancreatic endocrine lineage, shown as a percentage of the total cell population.

|  | TPB | ILV | TPB + Go6976 |
| --- | --- | --- | --- |
| Synaptophysin | 30.6% | 56.8% | 10.6% |
| INS | 12% | 3% | — |
| GCG | 4.6% | 12.6% | 3.1% |
| INS/GCG | 7.1% | 12.9% | 4% |

Example 2

An Alternative Method for the Formation of a Population of Cells Expressing Markers Characteristic of the Pancreatic Endocrine Lineage that Co-Express Insulin and NKX6.1 and Minimal Amounts of Glucagon In a separate experiment, cells of the human embryonic stem cells line H1 were cultured on MATRIGEL® (1:30 dilution) coated dishes with RPMI medium+0.2% FBS+100 ng/ml activin A+20 ng/ml WNT-3a for one day followed by treatment with RPMI media+0.5% FBS+100 ng/ml activin A for an additional two days (Stage 1), then DMEM/F12+2% FBS+50 ng/ml FGF7 for three days (Stage 2), then Treatment 8: DMEM-High glucose+1% B27+50 ng/ml FGF7+0.25 μM Cyclopamine-KAAD+2 μM Retinoic acid (RA)+100 ng/ml of Noggin+20 ng/ml Activin A+a p38 kinase inhibitor (disclosed in U.S. Pat. No. 6,214,830, at 2.5 μM) for four days (Stage 3, Treatment 8), or Treatment 9: DMEM-High glucose+1% B27+0.25 μM Cyclopamine-KAAD+2 μM Retinoic acid (RA)+100 ng/ml of Noggin for four days (Stage 3, Treatment 9), then DMEM-High glucose+1% B27+100 ng/ml Noggin+1 μM ALK5 inhibitor II+500 nM TPB for six days (Stage 4).

Stage 3, Treatment 8 resulted in the formation of a population of cells expressing markers characteristic of the pancreatic endoderm lineage that co-expressed PDX1 and NKX6.1, but did not express CDX2 and NGN3. On the other hand, stage 3, treatment 9 resulted in the formation of a population of cells expressing markers characteristic of the pancreatic endoderm lineage that co-expressed PDX1, NKX6.1 and NGN3. The effects of treatment with protein kinase C activator treatment on these cell populations were examined (Stage 4 above).

FACS analysis was performed to ascertain the percentage of insulin single positive cells, glucagon single positive cells, insulin/glucagon double positive cells, cells expressing NKX6.1 positive cells, insulin/NKX6.1 positive cells, and synaptophysin positive cells (a pan endocrine marker).

As shown in Table 3, the cell population formed with Treatment 8 gave rise to a larger percentage of endocrine cells, as denoted by synaptophysin expression: 49.7% of the total cell population expressed synaptophysin. 27.8% of the total population was insulin single positive cells.

On the other hand, the cell population formed with treatment 9 only gave rise to 25.7% synaptophysin expressing cells. 7.6% of the total population was single insulin-expressing cells. No significant difference of single glucagon expressing cells was observed in both treatments and the percentage of glucagon expressing cells was significantly lower than the insulin expressing cells.

A significant amount of insulin-expressing cells also co-expressed NKX6.1. In populations of cells that received treatment 8, 11% of the total population expressed insulin and NKX6.1. In populations of cells that received treatment 9, 2% of the total population expressed insulin and NKX6.1.

Figure 6:
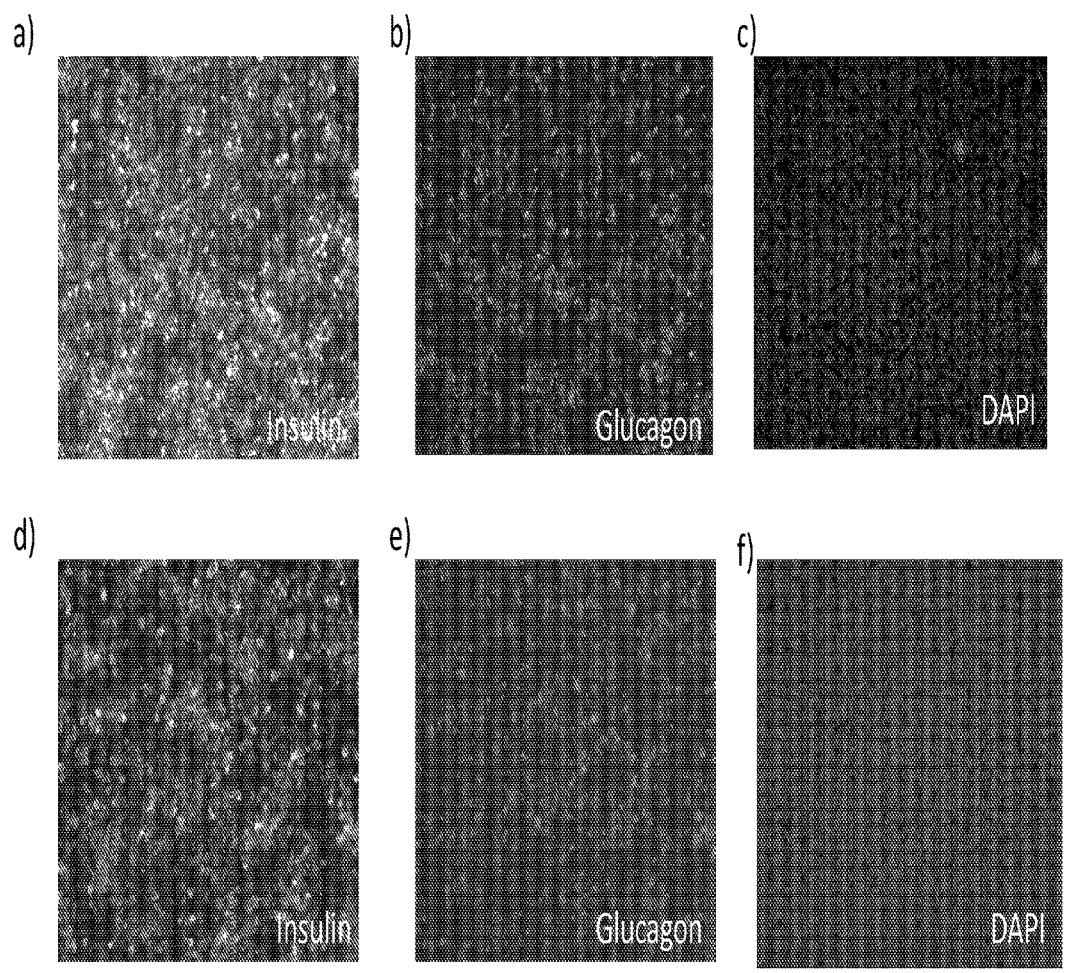
FIG. 6 shows the expression of insulin and glucagon in cells treated according to the methods of the present invention. Panels a to c show insulin expression (panel a), glucagon expression (panel b) and DAPI staining (panel c) in cells treated with DMEM-High glucose+1% B27+50 ng/ml FGF7+0.25 µM Cyclopamine-KAAD+2 µM Retinoic acid (RA)+100 ng/ml of Noggin+20 ng/ml Activin A+a p38 kinase inhibitor (disclosed in U.S. Pat. No. 6,214,830, at 2.5 µM) for four days (Stage 3, Treatment 8, Example 2). Panels d to f show insulin expression (panel d), glucagon expression (panel e) and DAPI staining (panel f) in cells treated with DMEM-High glucose+1% B27+0.25 µM Cyclopamine-KAAD+2 µM Retinoic acid (RA)+100 ng/ml of Noggin for four days (Stage 3, Treatment 9, Example 2).

Immunofluorescent analysis confirmed the above (FIG. 6). Treatment 8, resulted in an increase of insulin expressing cells comparing to Treatment 9 (FIG. 6 panel a and d). Most glucagon expressing cells were poly-hormonal cells (FIG. 6, panel a, b, d and e). These results suggest that the population of cells generated by treatment 8 (cells expressing makers characteristic of the pancreatic endoderm lineage that co-expressed PDX1 and NKX6.1, but did not express CDX2 and NGN3) can be more efficiently induced to become mature and functional insulin expressing cells by the methods of the present invention.

TABLE 3

Expression of markers characteristic of the pancreatic endocrine lineage, shown as a percentage of the total cell population.

|    | Synaptophysin | Insulin | Glucagon | Insulin/Glucagon | NKX6.1 | NKX6.1/Insulin |
|----|---------------|---------|----------|------------------|--------|----------------|
| T8 | 49.7%         | 27.8%   | 2.0%     | 16.4%            | 44.2%  | 11.0%          |
| T9 | 25.7%         | 7.6%    | 2.5%     | 4.9%             | 61.7%  | 2.0%           |

Example 3

An Alternative Method for the Formation of a Population of Cells Expressing Markers Characteristic of the Pancreatic Endocrine Lineage that Co-Express Insulin and NKX6.1 and Minimal Amounts of Glucagon In another experiment, cells of the human embryonic stem cells line H1 were cultured on MATRIGEL® (1:30 dilution) coated dishes with RPMI medium+0.2% FBS+100 ng/ml activin A+20 ng/ml WNT-3a for one day followed by treatment with RPMI media+0.5% FBS+100 ng/ml activin A for an additional two days (Stage 1), then
  DMEM/F12+2% FBS+50 ng/ml FGF7 for three days (Stage 2), then
  DMEM-High glucose+1% B27+50 ng/ml FGF7+0.25 µM Cyclopamine-KAAD+2 µM Retinoic acid (RA)+100 ng/ml of Noggin+20 ng/ml Activin A+a p38 kinase inhibitor (JNJ3026582, at 2.5 µM) for four days (Stage 3), then
  Treatment 10: DMEM-High glucose+1% B27+100 ng/ml Noggin+1 µM ALK5 inhibitor II+500 nM TPB for six days (Stage 4, Treatment 10), or
  Treatment 11: DMEM-High glucose+1% B27+100 ng/ml Noggin+1 µM ALK5 inhibitor II+500 nM TPB for nine days (Stage 4, Treatment 11), or
  Treatment 12: DMEM-High glucose+1% B27+100 ng/ml Noggin+1 µM ALK5 inhibitor II+500 nM TPB for twelve days (Stage 4, Treatment 12)

As shown in Table 4, when the duration of the protein kinase C activator treatment was extended to either nine days (Treatment 11) or twelve days (Treatment 12), no additional benefit was observed. Single insulin-expressing cells were 27.8% of the total population after six days treatment with Treatment 10. Conversely, insulin-expressing cells decreased to 10% after nine days treatment (Treatment 11), and declined further to 4% after twelve days treatment (Treatment 12). In parallel, the total percentage of insulin and NKX6.1 co-expressing cell population also dropped significantly after extending the treatment. These results suggested that a six day treatment with Noggin, Alk5 inhibitor II and a protein kinase C activator was sufficient enough to form the cells of the present invention.

Example 4

Implantation of the Cells of the Present Invention into Severe Combined Immunodeficient (SCID)—beige (Bg) Mice Cells of the human embryonic stem cells line H1 were cultured on MATRIGEL® (1:30 dilution)-coated dishes with RPMI medium+0.2% FBS+100 ng/ml activin A+20 ng/ml WNT-3a for one day followed by treatment with RPMI media+0.5% FBS+100 ng/ml activin A for an additional two days (Stage 1), then,
  DMEM/F12+2% FBS+50 ng/ml FGF7 for three days (Stage 2), then
  DMEM-High glucose+1% B27+50 ng/ml FGF7+0.25 µM Cyclopamine-KAAD+100 ng/ml Noggin for four days (Stage 3), then
  DMEM-High glucose+1% B27+100 ng/ml Noggin+1 µM ALK5 inhibitor II+500 nM TBP for six days (Stage 4).

Figure 7:
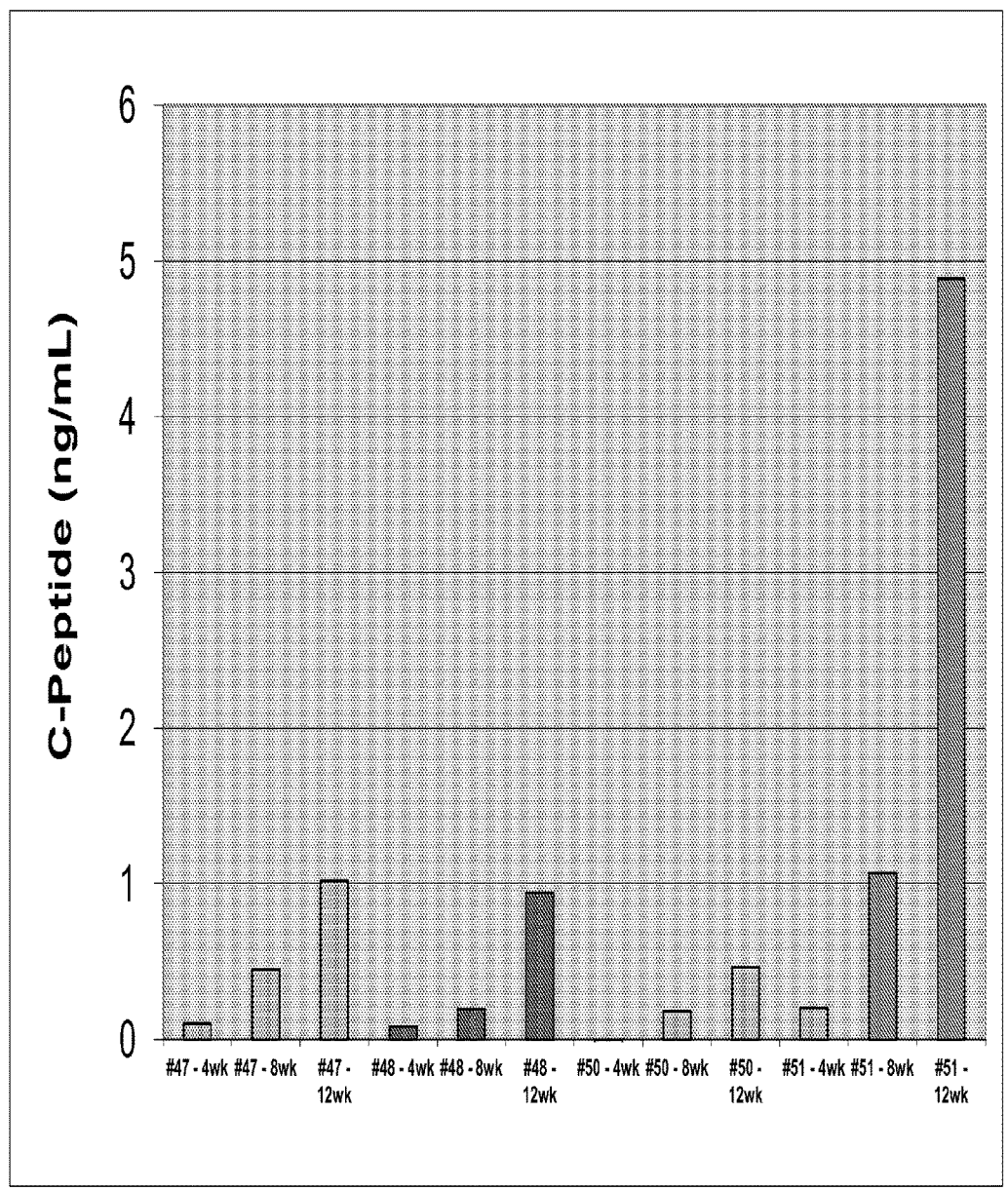
FIG. 7 shows human C-peptide was detected in (SCID)—beige (Bg) mice four, eight and twelve weeks after receiving the cells of the present invention, following a glucose challenge.

Cells at the end of stage four were mechanically scored using a 1-ml glass pipette and subsequently transferred to non-adherent plates for culture overnight. The resulting cell aggregates were collected, and aggregates containing 5 million cells were transplanted into the kidney capsule of an immuno-compromised mice (SCID/Bg, animal Nos. 47. 48. 49, 50 and 51). See FIG. 7.

After four weeks, functionality of the insulin-producing cells in these grafts was tested by injecting animals with glucose to induce insulin secretion. The animals were fasted for about 15-20 hrs, after which a blood sample (pre-glucose) was withdrawn retro-orbitally. Each animal then received an intraperitoneal injection dose of approximately 3 g/kg of glucose in 30% dextrose solution, and blood was withdrawn at about 60 minutes post glucose infusion. Circulating human C-peptide was detected using in mouse serum using an ultra-sensitive human specific C-peptide ELISA plates (Cat No. 80-CPTHU-E01, Alpco Diagnostics, N.H.). The detection of human C-peptide indicates that insulin secretion is derived from the grafted cells.

Human C-peptide was detected in animal serum as early as 4 weeks after transplantation and increased over time. The transplantation data is summarized in FIG. 7. At the end of one month, we were able to detect the human C-peptide (less than 0.2 ng/ml) in response to glucose administration in 60% of the animals in the study group. Glucose stimulated serum level of human C-peptide increased 5 to 10 fold in three out

TABLE 4

Expression of markers characteristic of the pancreatic endocrine lineage, shown as a percentage of the total cell population.

|        | Synaptophysin | Insulin | Glucagon | Insulin/Glucagon | NKX6.1 | NKX6.1/Insulin |
|--------|---------------|---------|----------|------------------|--------|----------------|
| 6-day  | 49.7%         | 27.8%   | 2.0%     | 16.4%            | 44.2%  | 11.0%          |
| 9-day  | 43.5%         | 10.0%   | 6.6%     | 7.8%             | 33.5%  | 1.0%           |
| 12-day | 37.6%         | 4.4%    | 4%       | 6.3%             | 32.5%  | 1.0%           | of the four mice after four weeks. At twelve weeks post implantation, the average glucose-stimulated serum levels of human c-peptide in transplanted mice were greater than 1 mg/ml (n=4).

Example 5

An Alternative Method for the Formation of a Population of Cells Expressing Markers Characteristic of the Pancreatic Endoderm Lineage that Co-Express PDX1 and NKX6.1

Briefly, cells of the human embryonic stem cell line H1 were cultured on MATRIGEL® (1:30 dilution) coated dishes and RPMI medium supplemented with 0.2% FBS, 100 ng/ml activin A and 20 ng/ml WNT-3a for one day, followed by treatment with RPMI media supplemented with 0.5% FBS and 100 ng/ml activin A, for an additional two days (Stage 1), then
  DMEM/F12+2% FBS+50 ng/ml FGF7 for three days (Stage 2), then
  DMEM-High glucose+1% B27+0.25 µM Cyclopamine-KAAD+2 µM Retinoic acid (RA)+100 ng/ml of Noggin for four days (Stage 3), then
  DMEM-High glucose+1% B27+100 ng/ml Noggin+1 µM ALK5 inhibitor II+20 nM PMA, or 100 nM TPB, or 20 nM Phorbol-12,13-dibutyrate (PDBu) (Calbiochem, cat#524390) for six days (Stage 4)

As a control, separate populations of cells were treated with DMEM High glucose, supplemented with 1% B27, 100 ng/ml of Noggin and 1 µM ALK5 inhibitor II for six days (stage 4).

Figure 8:
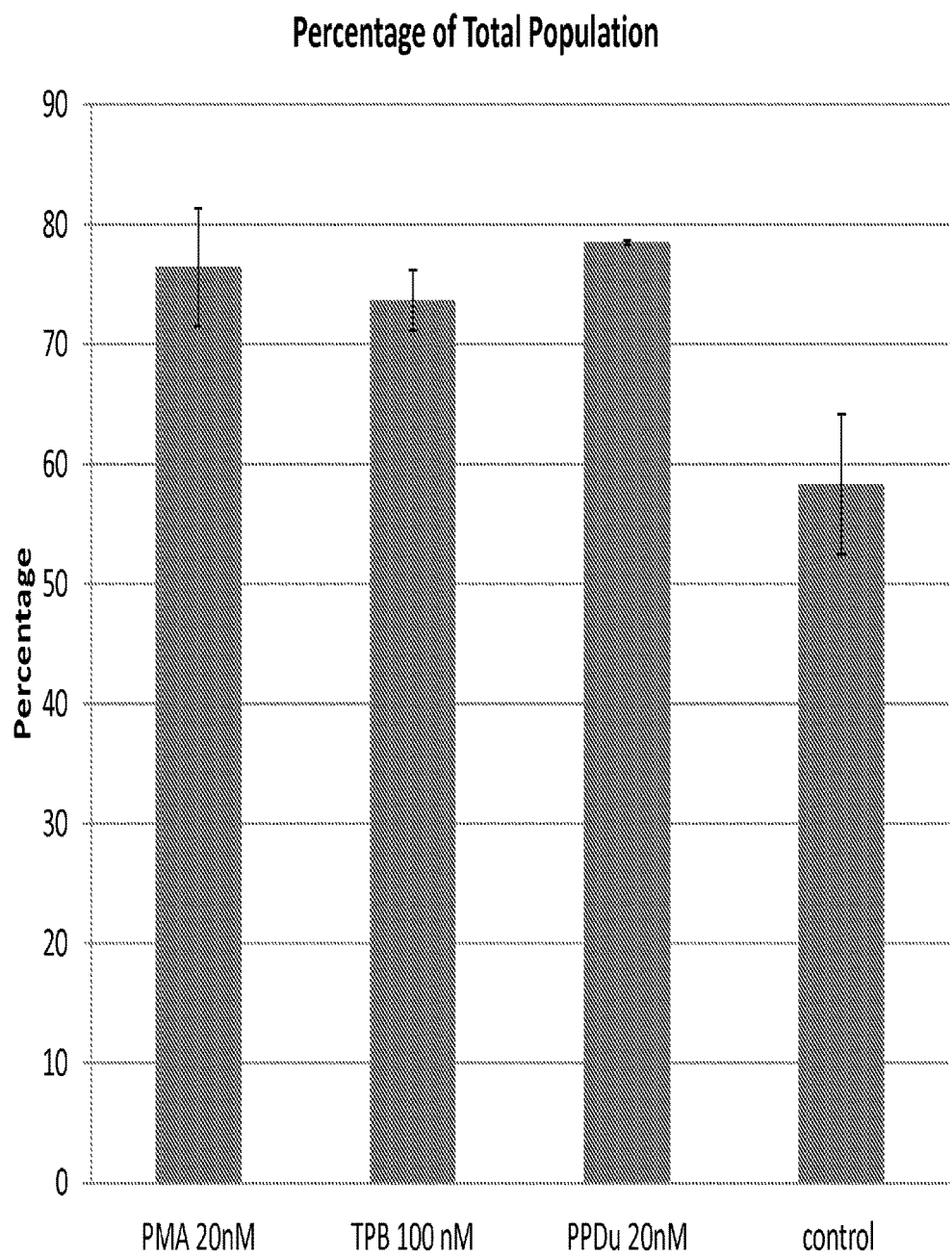
FIG. 8 shows the percentage of cells co-expressing PDX1 and NKX6.1 obtained following treatment of various protein kinase C inhibitors, at the concentrations indicated.

Cultures were sampled in duplicate on stage 4 day 6, and imaging was performed using an IN Cell Analyzer 1000 (GE Healthcare). Images from 100 fields per well were acquired to compensate for any cell loss during the bioassay and subsequent staining procedures. Measurements for total cell number, total PDX1 expressing cells and total NKX6.1 expressing cell were obtained from each well using IN Cell Developer Toolbox 1.7 (GE Healthcare) software. Averages and standard deviations were calculated for each replicate data set. Total PDX1 and NKX6.1 protein expressing cells was reported as percentage of the total cell population. As shown in FIG. 8, there was a dramatic increase of NKX6.1/PDX1 expressing cell population in the protein kinase C activator treated groups at a lower effective concentration (approximately 20 nM), compared to samples obtained from the control treatment. By day 6 of Stage 4, in populations of cells that received either protein kinase C activator or control treatment, 92%±4% of the population expressed PDX1. In the protein kinase C activator treated group, 75%±5% PDX1-expressing cells expressed NKX6.1. However, in populations only treated with Noggin and TGF beta receptor inhibitor (control), only 58%±5% of the PDX1-expressing cells expressed NKX6.1. In the presence of protein kinase C activator, 20% NKX6.1-expressing cells were co-positive with proliferation marker, EdU (Click-iT® EdU Imaging Kit, Invitrogen, Cat#C10337).

This example demonstrates that a protein kinase C activator can be used in combination with Noggin and TGF beta receptor inhibitor at a relatively low effective concentration (~20 nM) to facilitate the up-regulation of Nkx6.1 expression, and increase the percentage of cells expressing PDX1 and NKX6.1.

Example 6

Treatment of Cells Expressing Markers Characteristic of the Pancreatic Endoderm Linage with Protein Kinase C Activators Briefly, cells of the human embryonic stem cell line H1 were cultured on MATRIGEL® (1:30 dilution) coated dishes and RPMI medium supplemented with 0.2% FBS, 100 ng/ml activin A and 20 ng/ml WNT-3a for one day, followed by treatment with RPMI media supplemented with 0.5% FBS and 100 ng/ml activin A, for an additional two days (Stage 1), then
  DMEM/F12+2% FBS+50 ng/ml FGF7 for three days (Stage 2), then
  T1: DMEM-High glucose+1% B27+0.25 µM Cyclopamine-KAAD+2 µM Retinoic acid (RA)+100 ng/ml of Noggin+FGF10 50 ng/ml for four days (Stage 3, T1) or,
  T2: DMEM-High glucose+1% B27+0.25 µM Cyclopamine-KAAD+2 µM Retinoic acid (RA)+100 ng/ml of Noggin+FGF10 50 ng/ml+100 nM TPB for four days (Stage 3, T2), then
  DMEM-High glucose+1% B27+100 ng/ml Noggin+1 µM ALK5 inhibitor II for six days (Stage 4)

Figure 9:
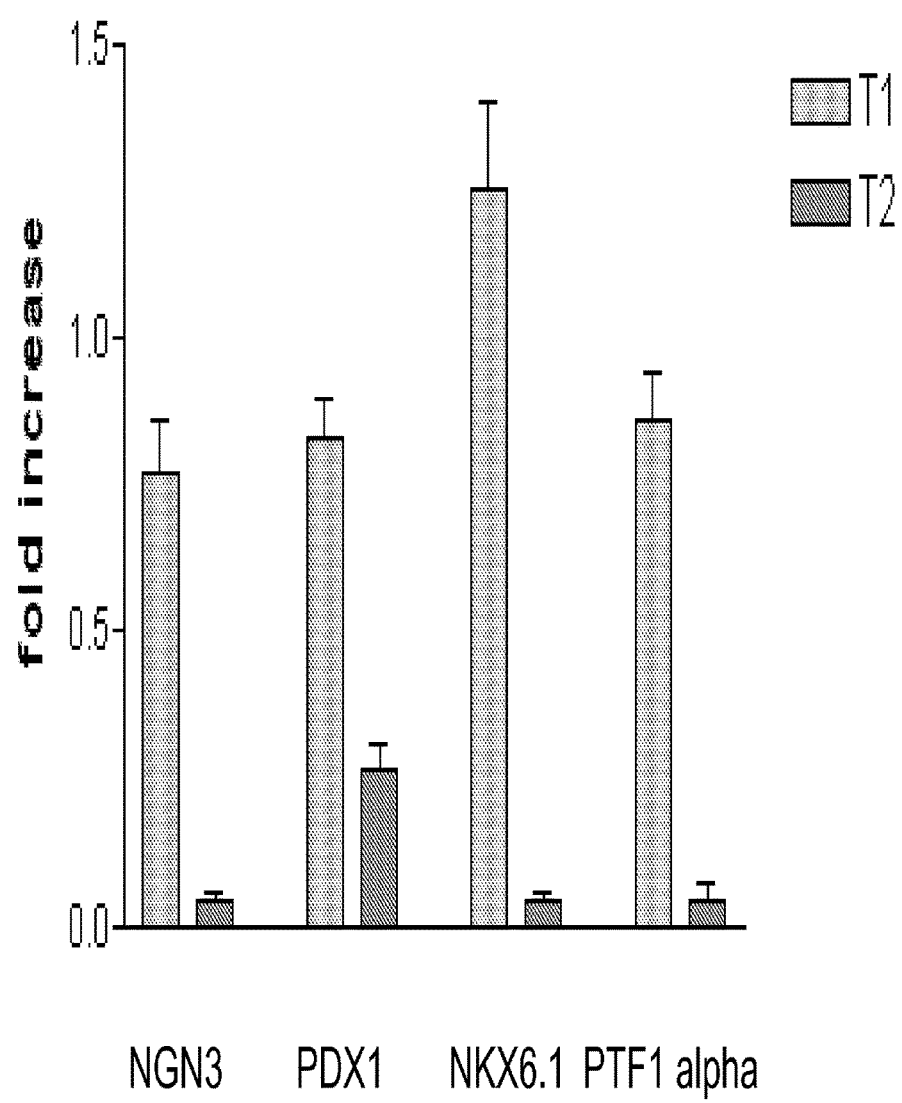
FIG. 9 shows the expression of NGN3, PDX1, NKX6.1 and PTF1 alpha in cells treated according to the methods described in Example 6.

As shown in FIG. 9, a significant down-regulation of the pancreatic endoderm markers PDX1, NKX6.1 and PTF1 alpha was observed, in cells treated with TPB (T2) compared to the control group (T1). NKX6.1 was undetectable by immunohistochemistry. These data suggest that protein kinase activator treatment at stage 3 did not facilitate the generation of PDX1/NKX6.1 co-expressing cells.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method of producing a population of NKX6.1 and insulin co-expressing human pancreatic endocrine cells comprising culturing human pancreatic endoderm cells in a medium supplemented with noggin, an inhibitor of ALK5, and a protein kinase C activator to obtain a population of NKX6.1 and insulin co-expressing human pancreatic endocrine cells, wherein less than 10% of the cells in the population express glucagon.

2. The method of claim 1, wherein the method comprises culturing for about 6 to about 12 days.

3. The method of claim 1, wherein the inhibitor of ALK5 is ALK5 inhibitor II.

4. The method of claim 1, wherein the protein kinase C activator is (2S, 5S)-(E, E)-8-(5-(4-(Trifluoromethyl)phenyl)-2,4-pentadienoylamino) benzolactam.

5. The method of claim 1, wherein at least 30% of the pancreatic endocrine cells express NKX6.1.

6. The method of claim 1, wherein at least 40% of the pancreatic endocrine cells express NKX6.1.

7. The method of claim 1, wherein at least 50% of the pancreatic endocrine cells express NKX6.1.

8. The method of claim 1, wherein at least 60% of the pancreatic endocrine cells express NKX6.1.

9. The method of claim 1, wherein at least 5% of the pancreatic endocrine cells express insulin.

10. A method of producing human pancreatic endocrine cells comprising culturing human pancreatic endoderm cells in a medium supplemented with noggin, an inhibitor of ALK5, and a protein kinase C activator and obtaining human pancreatic endocrine cells.

11. The method of claim 10, wherein less than 10% of the pancreatic endocrine cells in the population express glucagon.

12. The method of claim 10, wherein the method comprises culturing for about 6 to about 12 days.

13. The method of claim 10, wherein the inhibitor of ALK5 is ALK5 inhibitor II.

14. The method of claim 10, wherein the protein kinase C activator is (2S, 5S)-(E, E)-8-(5-(4-(Trifluoromethyl)phenyl)-2,4-pentadienoylamino) benzolactam.

15. The method of claim 10, wherein at least 30% of the pancreatic endocrine cells express NKX6.1.

16. The method of claim 10, wherein at least 40% of the pancreatic endocrine cells express NKX6.1.

17. The method of claim 10, wherein at least 50% of the pancreatic endocrine cells express NKX6.1.

18. The method of claim 10, wherein at least 60% of the pancreatic endocrine cells express NKX6.1.

19. The method of claim 10, wherein at least 5% of the pancreatic endocrine cells express insulin.

* * * * *